United States Patent
Tykocinski et al.

(10) Patent No.: US 6,797,489 B2
(45) Date of Patent: Sep. 28, 2004

(54) PP14 FUSION PROTEINS AND METHODS FOR MAKING AND USING THE SAME

(75) Inventors: Mark L. Tykocinski, Merion Station, PA (US); Gregory J. Riely, Cleveland Heights, OH (US)

(73) Assignee: TR Associates, L.L.C., Merion Station, PA (US)

( * ) Notice: Subject to any disclaimer, the term of this patent is extended or adjusted under 35 U.S.C. 154(b) by 198 days.

(21) Appl. No.: 10/169,687

(22) PCT Filed: Jan. 3, 2001

(86) PCT No.: PCT/US01/00104

§ 371 (c)(1),
(2), (4) Date: Oct. 29, 2002

(87) PCT Pub. No.: WO01/49163

PCT Pub. Date: Jul. 12, 2001

(65) Prior Publication Data

US 2004/0033231 A1 Feb. 19, 2004

Related U.S. Application Data

(60) Provisional application No. 60/174,287, filed on Jan. 3, 2000.

(51) Int. Cl.$^7$ ................................................ C12P 21/06

(52) U.S. Cl. .................... 435/69.1; 435/320.1; 435/325; 435/252.3; 514/2; 530/350

(58) Field of Search ............................. 435/69.1, 320.1, 435/325, 252.3; 514/2; 530/350

(56) References Cited

U.S. PATENT DOCUMENTS 6,001,596 A    12/1999   Hillman et al.

OTHER PUBLICATIONS

Anthony E. Bolton et al., Recombinant Genes Expressing PP14, European Patent Application Publication No. 0 658 624 A2, Published Jun. 21, 1995.
A. Amon et al., Placental Protein 13, International Patent Application Publication No. WO 99/38970, Published Aug. 5, 1999.

*Primary Examiner*—Karen Cochrane Carlson
(74) *Attorney, Agent, or Firm*—Debra Z. Anderson; Eckert Seamans Cherin & Mellott, LLC (57) ABSTRACT

Novel fusion proteins comprising PP14 are disclosed. The fusion proteins retain the immunoregulatory function of native PP14, but offer significant advantages. Methods for using the fusion proteins, and sequence encoding the same in the treatment of immune system diseases and disorders are therefore also disclosed, as are methods for recombinant production of the present fusion proteins.

26 Claims, 5 Drawing Sheets

PP14 FUSION PROTEINS AND METHODS FOR MAKING AND USING THE SAME

This application is a national stage application of PCT/US01/00104, filed Jan. 3, 2001, which claims benefit to U.S. provisional application 60/174,287, filed Jan. 3. 2000.

FIELD OF THE INVENTION

The present invention relates to novel fusion proteins comprising placental protein 14 (PP14) and methods for making and using these fusion proteins. The fusion proteins are useful for immune cell proliferation and function.

BACKGROUND INFORMATION

The human immune system functions to protect organisms from infection and from foreign antigens by cellular and humoral mechanisms. The immune system consists of cells and molecules that function in an orchestrated fashion to detect and eliminate foreign substances within the body. Though infectious agents, such as viruses, bacteria, parasites and fungi, represent the primary targets of the immune system, other aberrant cells within patients, such as infected, transplanted and cancerous cells, constitute additional immune targets. The abnormal molecules, largely proteins, of these various cellular and acellular targets of the immune system are generally referred to as antigens. The immune system is endowed with the capacity to seek out and destroy antigens. Essential operational features of the immune system are its abilities to recognize an enormously diverse array of antigens, distinguish one antigen from another in a highly specific fashion, and mount a more vigorous response when confronted with the same antigen more than once.

There are two major arms to the immune system, supported by different types of cells called B-lymphocytes and T-lymphocytes (B-cells and T-cells). B-cells make antibodies when they encounter antigens, and in most instances, these antibodies are protective. In autoimmune diseases, however, some of the antibodies react with the individual's tissues. When they deposit in tissue, they cause an inflammatory reaction and tissue damage. T-cells, like B-cells, are also activated when they encounter an antigen. As T-cells develop, they undergo a process called "thymic education." During thymic education, more than 95% of the T-cells die. The T-cells that have had a T-cell receptor that can recognize and react with the individual's own tissues (self antigens) are specifically eliminated. Some autoreactive T-cells escape the elimination process, however, and can initiate an immune response that results in autoimmune disease.

Autoimmune diseases are generally believed to result from inappropriate responses of the immune system. In many autoimmune diseases, the T-cells go astray and attack the body's healthy tissues. These T-cells appear to target the antigenic substances present in specific tissues. The antigenic substances differ depending upon the disease and may change in the course of the disease. In autoimmune diseases, the immune system appears to have escaped its normal control; what follows is a sequence of immune reactions that eventually lead to tissue damage. Autoimmune diseases are typically chronic and require life-long treatment. These treatments tend to fall into two categories: the first category involves compounds for palliative treatment, such as anti-inflammatory agents and pain killers; the second category involves the administration of nonspecific immunosuppressants, which indiscriminately shut down multiple parts of the immune system. These immunosuppressants usually have serious toxicity and side effect problems with long-term use and suppress the ability of the immune system to fight infection.

Thus, treatment of allergies and autoimmune diseases has been based on modalities that are toxic to immune cells, that inhibit production of antibodies, or that inhibit the effects of mediators of the immune response. Drugs that allow the manipulation of soluble lymphokines that regulate the immune system would be of use in the treatment of autoimmune diseases and diseases resulting from uncontrolled proliferation of immune cells. PP14 is one such drug of interest.

Pregnancy is a normal state in which at least one aspect of the immune response—reaction to foreign antigens—is suppressed in regard to paternal antigens expressed by the fetus. Reports dating back over a century have indicated that a substantial percentage of women with multiple sclerosis, rheumatoid arthritis and certain other autoimmune diseases experience complete or partial remission of disease symptoms in association with pregnancy, although disease manifestations recur postpartum. The expression of a variety of proteins, including PP14, is induced to high levels during pregnancy. PP14 is a major secretory protein of decidual tissue, where it comprises about 10% of the total soluble protein. PP14 is a naturally occurring protein detected at especially high levels in the amniotic fluid and blood of pregnant women, as well as in the seminal fluid of males. PP14 may account for at least some of the immune suppressive phenomena of pregnancy.

U.S. Pat. Nos. 5,039,521 and 5,256,411 disclose methods for treating immune system disorders in humans by administration of PP14, derivatives, fragments, or subunits thereof, or monoclonal antibodies thereto. Methods for inhibiting interleukin-1 are also disclosed. The '411 patent discloses a form of PP14 which is a dimer of two non-covalently linked protein subunits. Neither of the patents teach or suggest the PP14 fusion proteins disclosed herein.

PP14 has been shown to have in vitro effects on inflammatory cytokine (IL-1 and IL-2) production and T-cell proliferation. These immunoregulatory activities are evident at protein concentrations similar to those found in the serum of pregnant women. Investigations into the immunological function and regulation of PP14 have been impeded by the lack of recombinant PP14 derivatives with demonstrated ability to inhibit T-cell function. Because of PP14's immunoinhibitory capacity, stable and more effective forms of PP14 in the treatment of immune system disorders are desired.

SUMMARY OF THE INVENTION

The present invention is directed to a PP14 fusion protein for the treatment of immune system disorders. More specifically, the present invention is directed to a fusion protein comprising a first domain comprising one or more sequences of PP14, and a second domain comprising one or more sequences of the Fc portion of an immunoglobulin molecule, such as immunoglobulin IgG1. A preferred embodiment of this fusion protein is PP14·Fc$\gamma_1$. The present fusion proteins are recombinant derivatives that inhibit T-cell activation and, as discussed below, function in a manner superior to other forms of PP14. Methods for making and using the fusion proteins are also within the present scope.

The PP14 fusion proteins disclosed and claimed herein have been found to have unprecedented immunoregulatory capabilities. PP14 and its fusion proteins not only directly inhibit the activation of T-cells of the immune system, but do so by a unique "rheostatic" mechanism whereby they desensitize signaling through the T-cell receptor. As a consequence, they are effective in the modulation and treatment of autoimmune and alloimmune diseases. This may stem, at least in part, from their ability to skew T cell responses towards TH2 cytokine responses and away from TH1 cytokine responses. Because PP14 exists at high levels in the blood and amniotic fluid of pregnant women, and the fetus is therefore literally bathed in it without the slightest harmful effect, PP14 and its fusion proteins are not believed to have toxicity or significant side effects.

The present PP14 fusion proteins and genetic sequences encoding the same are useful in the treatment of a wide variety of immune and inflammatory diseases and conditions. The versatility of the PP14 fusion proteins is believed to address numerous autoimmune and alloimmune diseases by addressing the core pathogenic mechanism of those autoimmune diseases, although the inventor does not wish to be bound by this. Significantly, the present PP14 fusion proteins modulate the body's immune responses, versus shutting them down, as present autoimmune and alloimmune disease drugs do; this allows the body's immune system to continue to protect itself from opportunistic diseases and infections. Thus, the present invention provides for modulating the T-cell receptor response commensurate with the need to down regulate the cytokine output that is causing the immune system to inappropriately attack healthy cells, while at the same time allowing the immune system to protect the individual by retaining a sufficient degree of immune protection against infectious agents.

One aspect of the invention therefore is to provide PP14 in the form of fusion proteins.

Another aspect of the invention is to provide such proteins for use in the treatment of immune system diseases.

These and other aspects of the invention will be apparent based upon the following disclosure and appended claims.

BRIEF DESCRIPTION OF THE FIGURES

FIG. 1, including FIGS. 1A and 1B, shows the results of immunochemical characterization of the PP14·Fc$\gamma_1$ fusion protein, as determined by the methods of Example 1.

DETAILED DESCRIPTION OF THE INVENTION

The present invention is directed to a recombinant PP14 fusion protein. More specifically, the present invention is directed to a recombinant fusion protein comprising a first domain comprising a PP14 polypeptide sequence and a second domain comprising a polypeptide sequence of the Fc region or unit of an immunoglobulin protein.

Placental protein 14 (PP14), also known as glycodelin or progesterone-associated endometrial protein, is a 28 kDa glycoprotein with demonstrated T-cell inhibitory properties. The major source of PP14 is glandular cells of secretory and decidualized endometrium, and it is found in both the serum of pregnant women as well as their amniotic fluid, where it accumulates to high levels. PP14 has also been detected in seminal fluid, platelets and megakaryocytes, and tumor cell lines derived from breast, ovarian and hematopoietic lineages. PP14 is known to have immunosuppressive function. In contrast to most other immunosuppressive proteins, PP14 directly inhibits T-cells through a mechanism that is independent of accessory cells. In addition, PP14 is believed to impact upon an early phase of T-cell receptor-mediated T-cell activation, and thus may have a unique mechanism of action distinct from other T-cell suppressive factors.

PP14 itself may be obtained from a variety of sources, including mammalian placenta, mammalian blood, amniotic fluid, seminal plasma, cells and tissue culture, decidual cells, decidual organs, endometrial cells, endometrial organs and recombinant protein sources. PP14 cDNA, including human PP14 cDNA, can be commercially obtained from nucleotide sequence repositories or alternatively can be readily cloned by RT-PCR. The sequence listing for PP14 is set forth in U.S. Pat. No. 5,256,411, which is incorporated by reference herein. "PP14 polypeptide sequence" refers to this sequence, or any derivatives, fragment or subunit thereof that retains the biological activity of PP14. Thus, all polypeptide sequences of PP14 that retain their therapeutic activity are intended to be within the scope of the present invention, and domains encoding such sequences can be utilized in the present fusion proteins.

Any suitable Fc unit can be used in the present fusion proteins. Again, any derivative, fragment or subunit of an Fc unit can also be used, provided it retains the biological activity of the wild type Fc unit. Preferably, the Fc unit is the Fc unit of human IgG1 (Fc$\gamma_1$). This domain can be commercially obtained from the *American Type Culture Collection*, Mannassas, Va. and the sequence listing for the human IgG1 constant region can be found in Ellison, et al., *Nucleic Acids Research*, 10(13):4071–4079 (1982), hereby incorporated by reference in its entirety. Other suitable Fc units include IgG2a, IgG2b, IgG3, IgG4, IgM, IgA, and IgE.

The term "derivatives" as used herein in conjunction with the polypeptide sequences of PP14 and/or an Fc unit refers to PP14 or an Fc unit to which one or more amino acid residues have either been added or removed; it will be understood that such derivatives retain their biological function, and are therefore useful in the present invention. Modification of one or more amino acid residues of PP14 or an Fc unit by oxidation, reduction or other derivatization processes known in the art also results in PP14 or Fc unit derivatives, as that term is used herein.

Similarly, fragments and subunits of PP14 are useful in the treatment of human immune system disorders, provided that such portions retain their therapeutic activity. Fragments and subunits of an Fc unit are also useful in the present invention, provided they retain one or more of their functional properties, such as dimerization and/or protein A or protein G binding. "Fragments" and "subunits" of polypeptide sequences will be understood by those in the art as referring to a discrete portion of the protein that retains one or more of its functional properties or structural properties. For example, the PP14 protein fragment defined by amino acid residues 63 through 160 is believed to be a therapeutically active fragment of PP14 for purposes of the invention. This fragment includes four cysteine amino acids, which are believed to have biological activity. The fragment defined by amino acid residues 80 through 105 is also believed to be therapeutically active for purposes of the invention. The fragment defined by residues 80–105 is believed to be therapeutically active because: it is a linear sequence not involving disulfide bridges; the fragment contains a glycosylation site (at residues 85–87); the fragment has two tyrosine residues which, because of their phenyl side chains, may be involved in receptor interaction; and the double lysine sequence at residues 80–81 have double amino acid group activity, suggesting potential receptor activity.

The therapeutic activity of a derivative, fragment, or subunit of PP14 can be determined by its capacity to inhibit T-cell responses in standard functional assays, such as those taught by Rachmitewitz et al., *Cellular Immunology*, 191:26 (1999). Derivatives, fragments and subunits of PP14 that retain the physiological function of the wild type PP14 and are biologically active are within the scope of the present invention. The ability of a derivative, fragment or subunit of an Fc unit to dimerize can be determined by electrophoretic analysis, and to associate with protein A or protein G by affinity chromatography; such derivatives, fragments and subunits of an Fc unit are within the scope of the present invention. Thus, the terms "PP14 sequence", "PP14 polypeptide sequence" and "polypeptide sequence" "sequence" of the Fc portion of an immunoglobulin protein refer both to wild type PP14 and Fc sequences as well as biologically active derivatives, fragments and subunits thereof.

The term "recombinant" as used herein refers to the present PP14 fusion protein produced by recombinant DNA techniques, wherein the gene coding for PP14 and the gene coding for the Fc unit is cloned by recombinant DNA technology. One method for preparing a recombinant fusion protein according to the present invention therefore comprises: linking a first polynucleotide sequence encoding a PP14 protein, or derivatives, fragments or subunits thereof, to a second polynucleotide sequence encoding Fc polypeptide sequence to generate a chimeric coding sequence; subcloning the chimeric coding sequence into an expression vector; transfecting a cell with the expression vector; and purifying the fusion protein expressed by the transfected cell.

The PP14 sequence and the Fc unit sequence are as described above. Any suitable expression vector can be used including viral or nonviral vectors. Suitable nonviral vectors include, for example, plasmids, including self-replicating plasmids that incorporate Epstein Barr virus episomal replication elements, of which pREP7β is an example. Suitable viral vectors include, for example, lentivirus, adenovirus, adeno-associated virus, and herpes-simplex virus vectors. Any transfection means known in the art can be used for non-viral vectors, including lipofection, electroporation, and calcium-phosphate co-precipitation. The fusion protein generated by the transfected cells can be collected or purified from the cell medium by any means known in the art. Particularly preferred is protein A affinity chromatography, wherein a solid-phase matrix such as commercially available protein-A sepharose is used to immobilize the Fc fusion protein. The recombinant fusion protein thus produced can then be used in the treatment methods as reported herein.

The present fusion proteins can also contain one or more numerous other components that would enhance the utility of the present chimeric proteins, particularly in the areas of immunological study, animal models, diagnostics and therapeutics. For example, the proteins can be designed to contain an epitope tag. An epitope tag would be particularly useful in the laboratory setting to facilitate purification of the present proteins, to follow the localization of the proteins on cells or within populations of cells, and/or to enhance biological activity of the protein. For example, the primary sequence of either the first or second proteins can be altered through genetic engineering strategies to incorporate an epitope tag and thereby facilitate the biochemical isolation of the various proteins. A particularly useful alteration is the insertion of two or more neighboring histidine residues. This insertion can be, for example, in the amino or carboxy terminus of the peptide. Histidine residue insertion can be readily accomplished by the splice-by-overlap extension methodology, by incorporating histidine-encoding CAT and CAC triplet codons into the PCR primers at suitable locations in the coding sequence. Histidine-modified proteins can be efficiently and quantitatively isolated by the nickel-sepharose chromatography method. The histidine-nickel interaction is based upon protonation, and hence this interaction can be reversed, for purposes of peptide elution, through a simple pH shift. Other primary sequence modifications, such as the insertion of reactive amino acids for specific chemical coupling reagents, can also be performed. Alternatively, more conventional biochemical isolation strategies can be employed, including those based upon immunoaffinity. Other examples include the Flag epitope, which allows cross-linking of proteins, marker sequences and visualization sequences. For example, leucine zippers can be incorporated into the proteins in order to stabilize dimeric or trimeric complexes. Other moieties known to those skilled in the art that add to the function of the present fusion proteins can also be incorporated.

The present invention is also directed to a method for treating an immune system disorder in a patient by administering to the patient an effective amount of the recombinant fusion protein of the present invention. "Patient" refers to members of the animal kingdom, including but not limited to humans. "Immune system disease or disorder" as used herein refers to autoimmune, alloimmune, allergic, inflammatory or lymphoproliferative diseases or disorders. The term "autoimmune disease" more specifically refers to a heterogenous group of more than 80 serious, chronic illnesses that affect almost every human organ system, including the nervous, gastrointestinal, muscular skeletal, cardiovascular and endocrine systems. Autoimmune diseases, which may be crippling or fatal, can strike virtually any tissue or organ. Specific immune system disorders which may be treated according to the present method are arthritis, including rheumatoid arthritis and osteoarthritis, asthma, graft-versus-host disease, organ rejection, systemic lupus erythematosis, atopic allergy, multiple sclerosis, allergic dermatitis, inflammatory bowel disease, psoriasis, systemic sclerosis, sarcoidosis, and other inflammatory disorders. Lymphoproliferative disorders include but are not limited to malignant non-Hodgkin's lymphoma, Hodgkin's disease, or malignant histiocytosis. Autoimmune diseases manifested by infertility can also be treated according to the present methods. The immune system disorder may also be a neoplastic disorder, such as leukemia. Alloimmune disorders amenable to treatment are any one of a number of graft-versus-host and host-versus-graft reactions. Inhibition of IL-1, a major inflammatory mediator, is also within the scope of the present treatment methods.

An effective amount of the present recombinant fusion protein should be administered to the patient. The term "effective amount" refers to that amount of the fusion protein needed to bring about the desired response. Typically, the response will be alleviation, if not elimination, of one or more symptoms of the immune system disorder being treated, or, for example, inhibition of cytokine production. It will be understood that the effective amount needed for each patient will vary depending on such factors as the size of the patient, the condition of the patient's immune system and the patient's ability to mount an immune response, and the type and severity of the illness. The appropriate effective amount for each patient can be determined by one skilled in the art, but will generally be at least that amount which provides equivalent immunohibition to the native PP14 that is normally present in the blood of pregnant women (0.1–10 μM/L).

Administration can be by any method known in the art that is suitable for protein pharmaceuticals, such as intravenous injection, intramuscular injection, topical administration, oral ingestion, rectal administration, and inhalation. Alternatively, the present fusion proteins can be delivered directly to the site of inflammation, for example, intraarticular injection into an inflamed joint. The PP14 fusion proteins may be administered in admixture with a pharmaceutically acceptable carrier. Any such carrier can be used according to the present methods, as long as compatibility problems do not arise. A suitable pharmaceutically acceptable carrier is PBS.

The PP14 fusion proteins of the present invention retain the immunoregulatory properties of native PP14 in several notable respects. For example, the PP14 fusion proteins retain the ability to inhibit T-cell proliferation, particularly T-cell activation in response to anti-CD3 and anti-CD28 monoclonal antibodies. The present PP14 fusion proteins also have the ability to inhibit the secretion of cytokines, including interleukin-2 (IL-2) and indirectly interleukin-1 (IL-1).

Interleukin-1 (IL-1) is a peptide cytokine secreted by a variety of cell types and having a variety of functions, including an involvement in the activation of immune system T-cells. IL-1 also induces cartilage breakdown, leads to loss of proteoglycans from cartilage, induces bone resorption, is inflammatory, serves as a growth factor for lymphocytes, is a chemotactic factor and is a possible activator of polymorphonuclear leukocytes. When present in a sufficient concentration, IL-1 may cause fever, muscle wasting and sleepiness. IL-1 is a central mediator of inflammatory reactions and is important in the pathogenesis of chronic inflammatory diseases, of which rheumatoid arthritis (RA) is an example.

The present fusion proteins offer a significant advance over native PP14, in that the present fusion proteins, unlike native PP14, do not depend upon $\alpha_2$-macroglobulin ($\alpha_2 M$) for their immunoinhibitory function. $\alpha_2 M$ is the major serum carrier of PP14. While PP14 requires the presence of $\alpha_2 M$ for optimal immunological function, the present fusion proteins function independently of $\alpha_{2+} M$, and thus are functional, for example, in serum-free medium. Thus, the present fusion proteins may be even more attractive as both experimental tools and therapeutic agents than is native PP14. In addition, the present fusion proteins are more suitable than native PP14 as a therapeutic protein when injected into inflammatory sites lacking $\alpha_2 M$, for instance, inflamed joints.

While a preferred method of the present invention involves administration of a therapeutic fusion protein to a patient in need of said protein, an alternative treatment modality involves administration to said patient of a genetic sequence encoding the fusion protein of the present invention. "Genetic sequence" refers to a polynucleotide comprising the coding sequence for a defined protein and associated regulatory and other non-coding sequences. Genetic sequences in the form of cDNA clones are commercially available for a wide array of genes. Moreover, for those cDNA clones that are not readily accessible from commercial and other sources, knowledge of their nucleotide sequences can be used to easily reproduce their cDNAs via the reverse-transcriptase polymerase chain reaction method, incorporating the relevant gene sequence into the primers. This gene therapy approach is especially well-suited for patients requiring repeated administration of the therapeutic agent, since the exogenous genetic sequence can be incorporated into the patient's cells which will then produce the protein endogenously.

A broad array of methods for administering therapeutic genes to patients are well known in the art. These methods encompass a host of vectors for delivering therapeutic genes, a host of transcriptional and translational regulatory elements that can be appended to the gene of interest, methods for producing and using these vectors, methods for administering genes and vectors to patients, and methods for monitoring therapeutic gene efficacy and toxicity. A preferred embodiment involves intramuscular injection of a genetic sequence encoding a chimeric protein of the present invention. Once incorporated into the muscle cells of the patient, the encoded protein is produced and secreted systemically. The use of intramuscular gene therapy in this way for the treatment of autoimmunity is described in Chang, *J. Gene Medicine*, 1:415–423 (1999) and Piccirillo, *J. Immunology*, 161:3950–3956 (1998). An alternative embodiment involves local injection of the genetic sequence encoding a chimeric protein directly into a diseased site, for example, an inflammatory site, such as an inflamed joint. Lubberts, *J. Immunology*, 163:4546–4556 (1999) illustrates the direct intraarticular injection of a therapeutic gene into a knee joint in order to treat collagen-induced arthritis in an experimental animal.

Significantly, inducible promoters are known in the art for regulating the expression of the transfected gene, so that levels of the encoded protein can be regulated. Those inducible promoters that can be regulated with orally-administered drugs are especially useful in the context of the present invention. The genetic sequences of the present invention can be delivered to other organs, including liver, lung, and skin. Alternatively, the genetic sequences can be introduced into cells ex vivo by any one of a number of transfection modalities, and these transfected cells can be administered to a patient as therapeutic cells, according to methods well known in the art such as those reviewed in Tykocinski, *American Journal of Pathology*, 148:1–16 (1996). The use of transfected cells as therapeutic cells in this way for the treatment of experimental osteoarthritis is described in Pelletier, *Arthritis and Rheumatism*, 40:1012–1019 (1997), wherein transfected synovial cells were re-injected back into diseased joints. This is also illustrated by Yasuda, *J. of Clinical Investigation*, 102:1807–1814 (1998) who described the treatment of autoimmune diabetes with transfected islet cells.

EXAMPLES

The following examples are intended to illustrate the present invention and should not be construed as limiting the invention in any way.

Example 1

A PP14·Fcγ$_1$ fusion protein was produced using a chimeric cDNA expression construct incorporating the complete human PP14 coding sequence linked in-frame to sequences encoding the hinge, CH2 and CH3 constant domains of human IgG1. More specifically, human PP14 cDNA was amplified by polymerase chain reaction (PCR) using a 5' primer (5'-AAGCTTATGCTGTGCCT CCTGCTC3') and a 3' primer (5'-AAGCTT GTGAAACGGCACGGCTC-3'). The 5' primer introduced a Hind III site upstream of the PP14 coding sequence, while the 3' primer deleted the stop codon and introduced a Hind III site at the downstream end. The PP14 PCR fragment was ligated into the Hind III site of pIgG/REP7β vector according to the methods of Brunschwig, et al; *Journal of Immunology*, 155:5498 (1995), generating the expression plasmid pPP14·Fcγ$_1$/REP7β. Human 293 embryonic kidney cells (American Type Culture Collection, Manassas, Va.) were transfected with pPP14·Fcγ$_1$/REP7β using Lipofectin (Gibco-BRL, Gaithersburg, Md.) according to the manufacturer's protocol. After selection in 200 μg/ml hygromycin B (Calbiochem, La Jolla, Calif.), individual colonies were isolated. The conditioned media of hygromycin B-resistant clones were tested for secretion of the chimeric protein by a sandwich ELISA specific for human IgG1 (The Binding Site Ltd., Birmingham, UK). Conditioned media from pPP14·Fcγ$_1$/REP7β-transfected 293 cells was used to purify the fusion protein by protein A affinity chromatography. For scaled up production of pPP14·Fcγ$_1$, clones expressing high levels of PP14·Fcγ$_1$ were grown in Ultraculture (Bio Whitaker, Walkersville, Md.) containing 200 μg/ml hygromycin B. PP14·Fcγ$_1$ was purified from conditioned media according to the procedure used for other Fc fusion proteins as described by Bauer, et al., *European Journal of Immunology*, 27:1366 (1997). Briefly, conditioned media and an equal volume of Fc binding buffer (3.0 M sodium chloride, 1.5 M glycine, pH 8.6) were mixed with protein A-Sepharose (Sigma). After mixing overnight at 4° C., the matrix was collected and washed with 10 column volumes of 100 mM citrate pH 5.0. PP14·Fcγ$_1$ was eluted with 100 mM citrate, pH 3.0 into 0.4 volumes of 0.2 M sodium phosphate (dibasic). *Radioiodination of PP14.Fcγ$_1$*.

PP14·Fcγ$_1$ was radiolabeled by lactoperoxidase-catalyzed iodination. Briefly, 10 μg of protein were mixed with 1 mCi of Na[$^{125}$I] (NEN Life Sciences, Boston, Mass.) and 30 mu of lactoperoxidase (Calbiochem). The reaction was initiated by the addition of $H_2O_2$ ($4.2 \times 10^{-5}$%) and allowed to proceed for 15 seconds before being stopped with 0.05% sodium azide, 500 mM potassium iodide. Radiolabeled protein was separated from free iodine by gel filtration chromatography over G-25 Sephadex (Pharmacia, Piscataway, N.J.). The column elution buffer consisted of phosphate buffered saline (PBS) with 0.05% sodium azide and 0.1% bovine serum albumin. Immunoblot The purified PP14·Fcγ$_1$ fusion protein was tested by immunoblotting for reactivity with Ab specific for PP14 and human IgG1. Proteins were separated by 10% SDS-PAGE and electroblotted onto PVDF membranes which were probed with Ab specific for human IgG1 and rPP14, as described by Fayen, et al., *International Immunology*, 10:1347 (1998). Immunoblots were blocked overnight with 4% nonfat dried milk in PBS-T (PBS supplemented with 0.05% Tween 20). To detect the Fc domain, horseradish peroxidase (HRP)-conjugated antiserum specific for human IgG1 (1:1000; The Binding Site Ltd.) was used. Immunoblotting for PP14 was performed with rabbit anti-PP14 antiserum (1:3000) followed by HRP-conjugated goat anti-rabbit Ab (1:3000; Bio-Rad, Hercules, Calif.). Blots were developed by enhanced chemiluminescence reagent (DuPont-NEN, Boston, Mass.).

Figure 1:
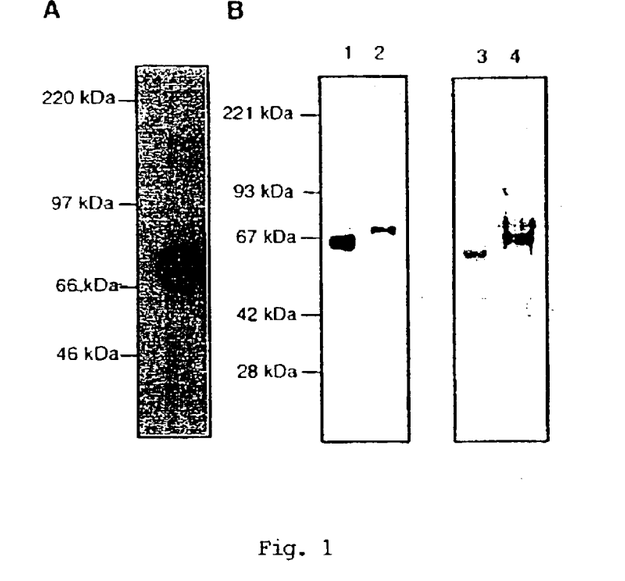

[$^{125}$I]-labeled purified PP14·Fcγ$_1$ was resolved by 10% SDS-PAGE and detected by autoradiography. As shown in FIG. 1A, the protein preparation consisted of a single homogeneous species with a molecular weight of about 70 kDa. FIG. 1B demonstrates the resolution of purified PP14·Fcγ$_1$ by 10% SDS-PAGE without (lanes 1 and 3) or with (lanes 2 and 4) β-mercaptoethanol and transferred to Immobilon-P membranes. The membranes were probed with polyclonal Abs specific for human IgG1 (lanes 1 and 2) or PP14 (lanes 3 and 4), and then detected by chemiluminescence. As shown in the figure, the positive immunoreactivity with both Ab verified the chimeric nature of the recombinant protein product.

Figure 2:
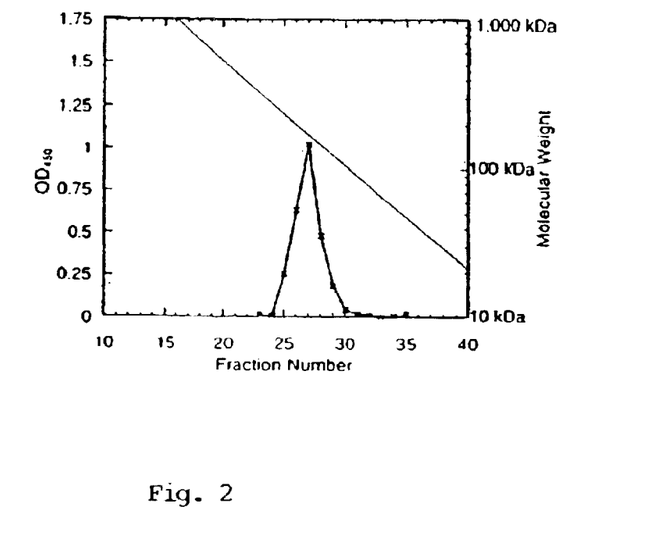
FIG. 2 shows the plot of IgG1 ELISA units vs. fraction number and molecular weight of the molecules eluting in each fraction, as determined by the methods of Example 1.

FIG. 2 shows the results of PP14·Fcγ$_1$ purification. Results are plotted as IgG1 ELISA units ($OD_{450}$). The dashed line and the right Y-axis indicate the approximate size of molecules eluting in each fraction after separation on a Superdex-200 gel filtration column. PP14·Fcγ$_1$ eluted at a column fraction corresponding to a globular protein molecular weight of 140–160 kDa, consistent with a dimeric complex composed of two 70 kDa subunits. T-Cell Proliferation Assay The effects of recombinant PP14·Fcγ$_1$ and native amniotic-PP14 on T-cell proliferation were compared. Human peripheral blood mononuclear cells (PBMC) were obtained from healthy laboratory volunteers and isolated by Ficoll-Hypaque density gradient centrifugation. T-cells were purified by complement-mediated depletion (Lympho-Kwik T, One Lambda, Canoga Park, Calif.). To stimulate proliferation, T-cells ($1 \times 10^5$ cells/μl well) were cultured in complete RPMI or AIM-V (Gibco-BRL) in the presence of varying concentrations of solid-phase anti-CD3 mAb and soluble anti-CD28 mAb, in the presence or absence of PP14·Fcγ$_1$ or AF. The PP14 in amniotic fluid (AF) inhibits T-cell proliferation in a dose-dependent manner, although inhibition is abrogated at higher stimulus concentrations. About 1 μg/ml soluble anti-CD28 mAb (9.3; provided by Bristol-Myers Squibb) was added to stimulate proliferation. The proteins were immobilized on protein A-Sepharose (Sigma Chemical Co., St. Louis, Mo.). PP14·Fcγ$_1$ or AF was added as described below. The T-cells were cultured for 72 h in a humidified 37° C., 5% $CO_2$ incubator. To measure proliferation, cells were pulsed with [$^3$H]-thymidine (2.5 μCi/ml) for the last 14–18 hours. Plates were harvested in a Harvester 96 (Tomtec, Orange, Conn.), and the incorporated [$^3$H] was analyzed on a 1205 Betaplate™ liquid scintillation counter (Wallac, Gaithesburg, Md.). Data presented are representative of at least three experiments performed in triplicate.

Figure 3:
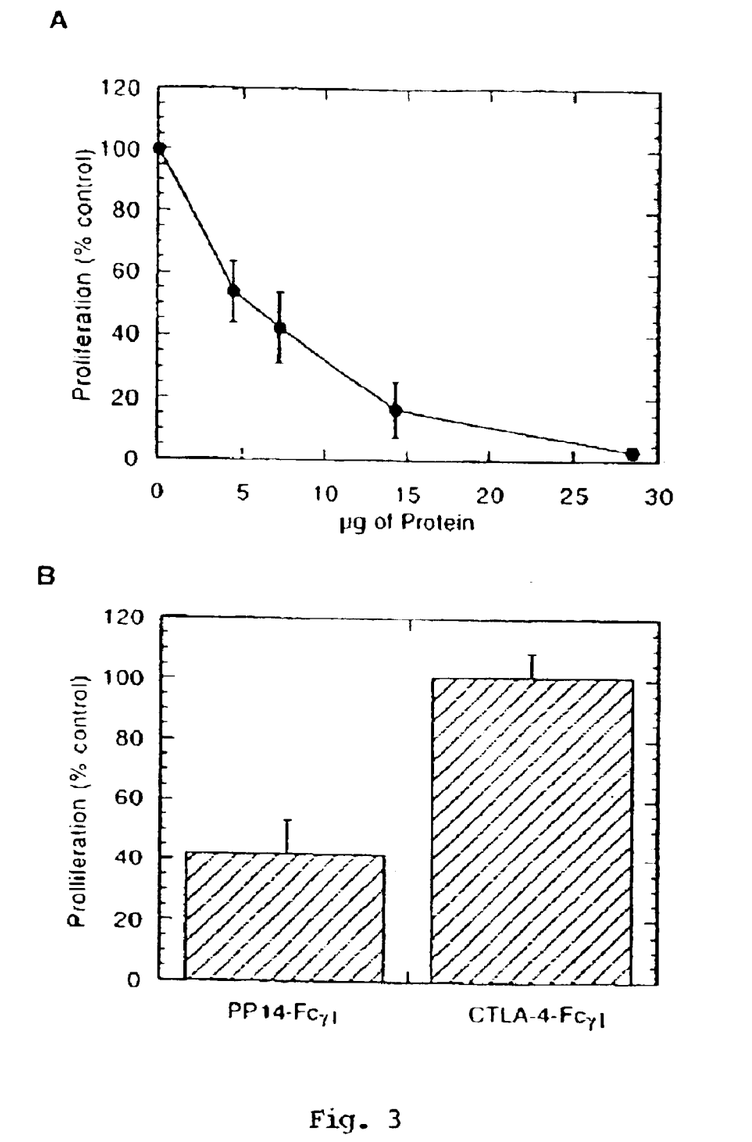
FIGS. 3A and 3B show T-cell proliferation against μg of PP14·Fc$\gamma_1$ protein (FIG. 3A) and graphs proliferation in the presence of PP14·Fc$\gamma_1$ and CTLA-4·Fc$\gamma_1$ (FIG. 3B), as determined by the methods of Example 1.

FIG. 3A (upper panel) shows the results of human peripheral blood T-cells stimulation with solid-phase anti-CD3 mAb (4 μg/ml) and soluble anti-CD28 mAb (1 μg/ml), in the presence of increasing amounts of PP14·Fcγ. FIG. 3B (lower panel) shows the proliferative inhibition of PP14·Fcγ$_1$ (left bar) venous CTLA-4·Fcγ$_1$ (right bar). Proliferation assessed by incorporation of [$^3$H]-thymidine is expressed as % of control (calculated as cpm) with indicated protein/cpm without added protein. PP14·Fcγ$_1$ inhibited T-cell proliferation in a dose-dependent manner. In contrast, a control fusion protein incorporating the same Fc sequence displayed no inhibitory effect. These data confirm that PP14·Fcγ$_1$ mimics native PP14 as a negative regulator of T-cell proliferation.

Example 2

Figure 4:
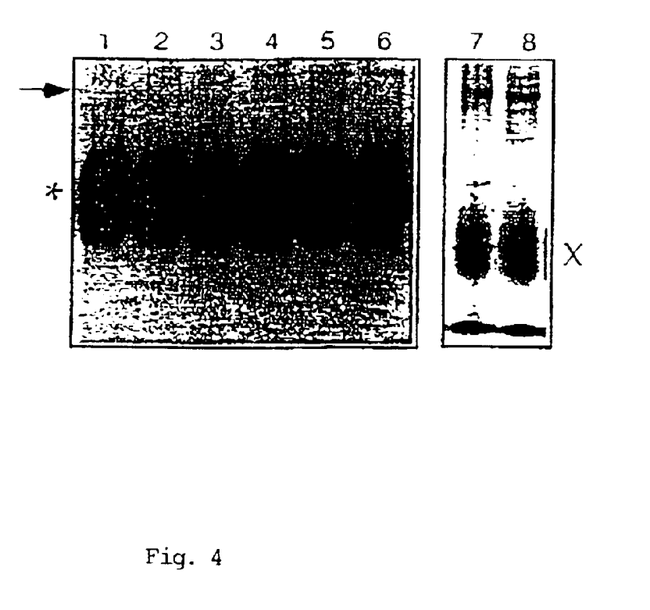
FIG. 4 demonstrates that PP14·Fc$\gamma_1$ does not bind to either $\alpha_2$M or MA-$\alpha_2$M, as determined by the methods of Example 2.

Characterization of PP14·Fcγ$_1$'s Susceptibility to α$_2$-Macroglobulin Regulation The serum carrier protein α$_2$-macroglobulin (α$_2$M), first described as a protease inhibitor, is now recognized for its ability to bind and modulate the activity of diverse growth factors and cyokines, including IL-2, TGFβ, PDGF, and NGF. α$_2$M binds to native PP14 and thereby potentiates PP14 's immunoinhibitory activity. This example tested whether α$_2$M also binds to recombinant PP14·Fcγ$_1$. To assess binding, $^{125}$I-labeled PP14·Fcγ$_1$, prepared as described above, was incubated in the absence (FIG. 4, lanes 1 and 4) or presence of purified human α$_2$M (lanes 2 and 3) or methylene activated α$_2$M (MA-α$_2$M) (lanes 5 and 6) for 3 h at 37° C. and separated by 5% native PAGE The addition of excess unlabeled PP14·Fcγ$_1$ did not influence migration patterns (lanes 3 and 6). As shown in FIG. 4, no binding of $^{125}$I-PP14·Fcγ$_1$ to either purified α$_2$M or MA-α$_2$M was detected. The arrow indicates the position of α$_2$M as determined by Coomassie Blue staining, and the asterisk indicates the position of free PP14·Fcγ$_1$.

Example 3

Figure 5:
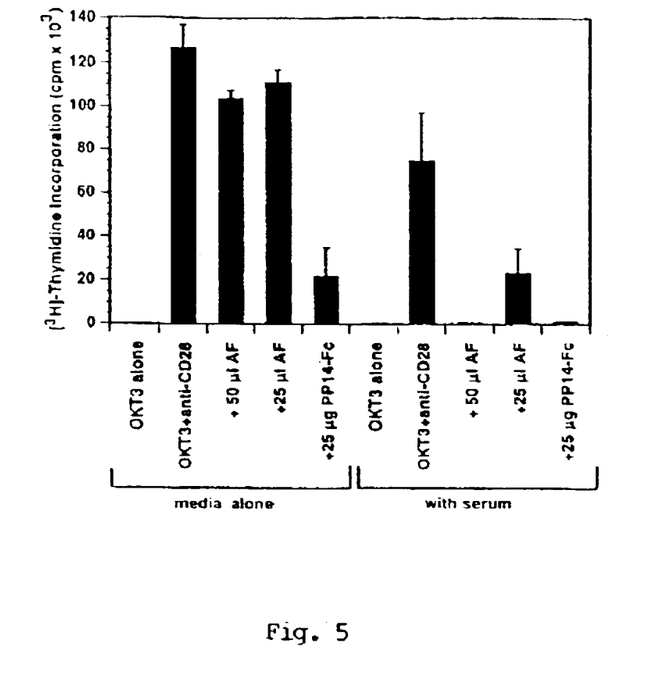
FIG. 5 shows that PP14·Fc$\gamma_1$ does not rely on $\alpha_2$M for its immunoinhibitory function, as determined by the methods of Example 3.

The ability of PP14·Fcγ$_1$ to inhibit T-cell proliferation in the absence of α$_2$M was directly tested. Purified human T-cells in serum-free conditions were stimulated with solid-phase anti-CD3 mAb (2 μg/ml) and soluble anti-CD28 mAb (9.3, final concentration 1 μg/ml), with or without 10% fetal bovine serum in the presence of 12.5% amniotic fluid or 12 μg PP14·Fcγ$_1$ Proliferation was assessed as described in Example 2. As shown in FIG. 5, both native PP14 (in amniotic fluid) and PP14·Fcγ$_1$ markedly inhibited T-cell proliferation in the presence of serum. In the absence of serum, however, the immunoinhibitory capacities of PP14 and PP14·Fcγ$_1$ diverged. While native PP14 's capacity to inhibit T-cell proliferation was dramatically reduced in the absence of serum, PP14·Fcγ$_1$ retained its immunoinhibitory potential under serum-free conditions, that is, culture conditions shown which α$_2$M is absent. Taken together, these data indicate that PP14·Fcγ$_1$, unlike native PP14, does not depend upon α$_2$M for its immunoinhibitory function. Data are representative of at least three experiments, each done in triplicate.

The above examples demonstrate the present methods for preparing recombinant fusion proteins comprising PP14 and an Fc region. The fusion protein recombinantly expressed functions in the same immunoregulatory manner as native PP14, and are therefore useful in the treatment of all immune system disorders as reported for native PP14. The present PP14 fusion proteins are even more attractive by virtue of their ability to function in the absence of α$_2$M.

Whereas particular embodiments of this invention have been described above for purposes of illustration, it will be evident to those skilled in the art that numerous variations of the details of the present invention may be made without departing from the invention as defined in the appended claims.

What is claimed is:

1. A recombinant fusion protein comprising a first domain comprising a placental protein 14 (PP14) polypeptide sequence and a second domain comprising a polypeptide sequence of the Fc region of an immunoglobulin.

2. The fusion protein of claim 1, wherein said Fc region is the Fc region of immunoglobin IgG1.

3. The fusion protein of claim 1 wherein said Fc region is selected from the group consisting of IgG2a, IgG2b, IgG3, IgG4, IgM, IgA and IgE.

4. The fusion protein of claim 2, wherein said Fc region is the multi-domain Fc region from a human immunoglobulin protein.

5. The fusion protein of claim 1, further comprising one or more of an epitope tag or a leucine zipper.

6. The fusion protein of claim 6, wherein said epitope tag is a polyhistidine tag.

7. A method for making the recombinant fusion protein of claim 1 comprising:
   linking a first polynucleotide sequence encoding a PP14 polypeptide sequence to a second polynucleotide sequence encoding a polypeptide sequence of the Fc region of an immunoglobulin protein, to generate a chimeric coding sequence;
   subcloning the chimeric coding sequence into an expression vector;
   transfecting a cell with said expression vector; and
   purifying the fusion protein expressed by the transfected cell.

8. The method of claim 7, wherein said second polynucleotide sequence encodes the multi-domain Fc region of human immunoglobulin IgG1.

9. The method of claim 7, wherein said expression vector is selected from the group consisting of a viral vector and a nonviral vector.

10. The method of claim 9, wherein said nonviral vector is a plasmid.

11. The method of claim 9, wherein said nonviral vector comprises Epstein Barr virus episomal replication elements.

12. The method of claim 11, wherein said expression vector is pREP7β.

13. The method of claim 5, wherein purification is effected by protein A or protein G affinity chromatography.

14. A method for treating an immune system disorder in a patient by administering to said patient an effective amount of the recombinant fusion protein of claim 1.

15. The method of claim 14, wherein said immune system disorder is selected from the group consisting of autoimmune, alloimmune, allergic, inflammatory and lymphoproliferative disorders.

16. The method of claim 14, wherein administration is by a method selected from the group consisting of intravenous injection, intramuscular injection, intraarticular administration, oral administration, topical administration, rectal administration, and inhalation.

17. The method of claim 14, wherein said immune system disorder is selected from the group consisting of arthritis, asthma, graft-versus-host disease, organ rejection, systemic lupus erythematosus, atopic allergy, inflammatory bowel disease, multiple sclerosis, systemic sclerosis, allergic dermatitis, psoriasis, autoimmune thyroiditis, autoimmune liver disease, and sarcoidosis.

18. The method of claim 14, wherein said immune system disorder is rheumatoid arthritis.

19. The method of claim 14, wherein said immune system disorder is a lymphoproliferative disorder.

20. The method of claim 19, wherein said lymphoproliferative disorder is selected from the group consisting of malignant non-Hodgkin's lymphoma, Hodgkin's disease, and malignant histiocytosis.

21. The method of claim 14, wherein said immune system disorder is a neoplastic disorder.

22. The method of claim 21, wherein said neoplastic disorder is leukemia.

23. The method of claim 14, wherein said effective amount is that amount necessary to achieve a PP14 concentration in the blood of at least 0.1 μM/L.

24. The method of claim 14, wherein said fusion protein is administered in admixture with a pharmaceutically acceptable carrier.

25. A method for inhibiting interleukin-1 production in a patient comprising administering to said patient an effective amount of the recombinant fusion protein of claim 1 in an amount effective to inhibit interleukin-1 production.

26. A method for inhibiting a TH1 cytokine response in a patient comprising administering to said patient an effective amount of the recombinant fusion protein of claim 1 in an amount effective to inhibit said response.

* * * * *